(12) United States Patent
Graumann

(10) Patent No.: US 8,944,680 B2
(45) Date of Patent: Feb. 3, 2015

(54) X-RAY FACILITY HAVING A RECORDING ARRANGEMENT HELD ON SUPPORT ARMS

(75) Inventor: Rainer Graumann, Höchstadt (DE)

(73) Assignee: Siemens Aktiengesellschaft, Munich (DE)

( * ) Notice: Subject to any disclaimer, the term of this patent is extended or adjusted under 35 U.S.C. 154(b) by 326 days.

(21) Appl. No.: 13/602,457

(22) Filed: Sep. 4, 2012

(65) Prior Publication Data

US 2013/0223597 A1    Aug. 29, 2013

(30) Foreign Application Priority Data

Sep. 2, 2011    (DE) .......................... 10 2011 082 075

(51) Int. Cl.
*A61B 6/00* (2006.01)
*G03B 42/02* (2006.01)
*A61B 19/00* (2006.01)

(52) U.S. Cl.
CPC ............. *A61B 6/4429* (2013.01); *A61B 6/4458* (2013.01); *A61B 6/4476* (2013.01); *A61B 6/4452* (2013.01)
USPC ........ 378/197; 378/196; 378/207; 250/491.1; 250/492.1; 250/492.3

(58) Field of Classification Search
USPC ............ 378/196, 197, 207; 250/492.1, 492.3, 250/491.1
See application file for complete search history.

(56) References Cited

U.S. PATENT DOCUMENTS

| | | | | |
|---|---|---|---|---|
| 4,541,108 A | * | 9/1985 | Grady et al. | 378/196 |
| 4,653,083 A | * | 3/1987 | Rossi | 378/196 |
| 4,879,737 A | * | 11/1989 | Grady | 378/196 |
| 4,987,585 A | * | 1/1991 | Kidd et al. | 378/197 |
| 6,382,833 B2 | * | 5/2002 | Leandersson et al. | 378/197 |
| 6,435,714 B1 | * | 8/2002 | Bruder | 378/196 |
| 6,435,715 B1 | | 8/2002 | Betz et al. | |
| 6,895,268 B1 | * | 5/2005 | Rahn et al. | 600/429 |
| 7,193,227 B2 | * | 3/2007 | Hiramoto et al. | 250/492.3 |
| 7,460,636 B2 | * | 12/2008 | Ein-Gal | 378/9 |
| 7,534,036 B2 | * | 5/2009 | Delmas et al. | 378/196 |
| 7,638,779 B2 | * | 12/2009 | Herrmann | 250/491.1 |
| 7,789,562 B2 | * | 9/2010 | Strobel | 378/207 |
| 7,899,223 B2 | * | 3/2011 | Boese et al. | 382/128 |
| 2001/0053201 A1 | * | 12/2001 | Leandersson et al. | 378/195 |
| 2003/0219102 A1 | * | 11/2003 | Mitschke et al. | 378/207 |
| 2008/0101546 A1 | * | 5/2008 | Delmas et al. | 378/197 |
| 2009/0185657 A1 | * | 7/2009 | Klingenbeck-Regn | 378/14 |
| 2009/0204032 A1 | * | 8/2009 | Herrmann et al. | 601/4 |
| 2010/0008474 A1 | | 1/2010 | Hornung et al. | |
| 2012/0213338 A1 | * | 8/2012 | Hartwich et al. | 378/197 |
| 2012/0257725 A1 | * | 10/2012 | Noda | 378/197 |
| 2013/0202093 A1 | * | 8/2013 | Meyer et al. | 378/197 |
| 2013/0223597 A1 | * | 8/2013 | Graumann | 378/197 |

FOREIGN PATENT DOCUMENTS

DE    19855213 C2    3/2001
DE    102008032294 A1    1/2010

* cited by examiner

*Primary Examiner* — David A Vanore
(74) *Attorney, Agent, or Firm* — Laurence A. Greenberg; Werner H. Stemer; Ralph E. Locher

(57) ABSTRACT

An X-ray facility has at least one x-ray emitter, an x-ray detector and an isocenter arranged along a central beam path between the x-ray emitter and the x-ray detector. The x-ray emitter and the x-ray detector are arranged on separate support arms. At least one rotary device is provided on each support arm, by way of which the x-ray emitter or the x-ray detector can be rotated about an axis of rotation intersecting the isocenter and not corresponding to the central beam. Wherein the axes of rotation match rotary devices assigned to one another on different support arms.

18 Claims, 1 Drawing Sheet

X-RAY FACILITY HAVING A RECORDING ARRANGEMENT HELD ON SUPPORT ARMS

CROSS-REFERENCE TO RELATED APPLICATION

This application claims the priority, under 35 U.S.C. §119, of German application DE 10 2011 082 075.2, filed Sep. 2, 2011; the prior application is herewith incorporated by reference in its entirety.

BACKGROUND OF THE INVENTION

Field of the Invention

The invention relates to an x-ray facility including at least an x-ray emitter, an x-ray detector and an isocenter arranged along the central beam between the x-ray emitter and the x-ray detector.

X-ray facilities are currently widely known in the prior art. Here the core of an x-ray facility is in most cases the recording arrangement, which includes the x-ray emitter and the x-ray detector. The x-ray emitter and x-ray detector are usually fixed opposite one another. If the central beam of the x-ray emitter is considered, this usually strikes the center of the x-ray detector, at least in a basic position, thereby frequently being referred to as central beam and being used to define the further geometry of the x-ray facility. The central beam traverses the isocenter of the x-ray facility, in isocentric x-ray facilities (in particular isocentric C-arms), in which an object to be recorded is usually arranged. In this way the isocenter is usually located in the center of the central beam. X-ray facilities are however also known, which have no isocenter, but their central beam moves instead about the rotational center point during rotations on an ellipsis for instance.

Different types of x-ray facilities, which offer a certain degree of flexibility in terms of positioning the recording arrangement, are already known in the prior art. It was therefore proposed to arrange the x-ray emitter and the x-ray detector opposite one another on arms of a C-arm. The C-arm may then have several degrees of freedom, in order to be set for a plurality of recording geometries. Advantages of C-arm x-ray facilities are the simple operability, its low weight and mobility as well as its universal and flexible usability. Disadvantageously x-ray facilities with C-arms nevertheless have restricted mobility and are relatively mechanically unstable.

Robotic systems were also proposed, in which a C-arm is arranged on a robot arm for instance thereby providing here for greater flexibility with greater precision and a wide application spectrum. Disadvantageously robotic systems are however expensive, bulky and extremely complicated in terms of operation.

SUMMARY OF THE INVENTION

The object underlying the invention is therefore to specify an x-ray facility, which is improved in terms of mechanical and dynamic properties, in particular in respect of stability and flexibility.

To achieve this object, in an x-ray facility of the type cited in the introduction, provision is made in accordance with the invention for the x-ray emitter and x-ray detector to be arranged on separate support arms. At least one rotary device is provided on each support arm, by way of which the x-ray emitter and the x-ray detector can be rotated about an axis of rotation intersecting the isocenter and not corresponding to the central beam, wherein the axes of rotation correspond to rotary device assigned to one another on different support arms.

Provision is therefore made in accordance with the invention to provide support arms which are not fixedly mechanically coupled to one another, and are consequently separate, for the x-ray emitter and the x-ray detector, which have at least one rotational degree of freedom, which does not correspond to the central beam in the axis of rotation. Since the axes of rotation do not correspond to the central beam, this means that the x-ray detector and x-ray emitter are moved translationally in the space by the rotary devices. Since the axes of rotation now also always intersect the isocenter in each instance and two rotary devices on different support arms are assigned in each instance, in other words their axes of rotation match one another, it is now possible to change the position of the x-ray emitter and x-ray detector in the space by simple rotations such that the basic geometry is consequently retained, which means that the central beam also traverses the isocenter between the components x-ray emitter and x-ray detector arranged opposite one another thereby rendering x-ray recordings possible. In this context, provision can be made particularly advantageously for the x-ray facility to include at least one movement coupling facility for at least one pair of rotary devices assigned to one another, which when rotating the one rotary device about a specific angle is embodied to rotate the other rotary device in the same direction about the specific angle. The rotary device can therefore basically already be coupled such that an essentially useable recording geometry is preserved.

A completely new design and a completely new mechanism for a flexibly useable x-ray facility are overall specified in accordance with the invention, by support arms being provided, which allow for changeability of the spatial position of the x-ray emitter and x-ray detector by way of rotational movements. In this way the x-ray emitter and x-ray detector always run on a spherical surface. It is possible in this way for the movement to be realized mainly, in particularly exclusively or almost exclusively, for instance up to one (shared) height adjustment of the support arms, by rotating the rotary device(s), so that high stability, reproducibility and flexibility are achieved. With a suitable design, in particular using suitable axes of rotation with several pairs of rotary devices, embodiments, which are explained in further detail below, can be provided in which any positions can be moved into and any paths can be realized for the x-ray detector and the x-ray emitter.

This high flexibility and stability has proven useful particularly in respect of surgical operation environments, if an imaging accompanying an intervention is to take place for instance. It is then possible to control the support arms such that an image recording is possible, without excessive hindrances when accessing a patient or suchlike. Advantages also result in respect of the three-dimensional imaging (C-arm CT) and in this case the complex recording geometries to be run. Furthermore, the present invention provides to enable a 3D imaging on any predeterminable trajectories, up to a near-360° rotation, which is addressed in further detail below.

In a particularly advantageous embodiment of the present invention, provision can be made to provide at least two pairs of coupled rotary devices with axes of rotation pointing in different directions. As already mentioned, it is basically conceivable, given suitable selection of axes of rotation, to allow almost or all arbitrary positions of the x-ray detector and x-ray emitter in the space. Provision can be made for instance for two axes of rotation of the pairs to exist tilted by 45 degrees to one another. As already mentioned, the axes of rotation of pairs of rotary devices always point towards the isocenter, which ensures that the central beam always runs through the isocenter between the x-ray emitter and the x-ray detector, irrespective of the position of the rotary device. In this process, as mentioned, it need only be ensured that (equivalent) rotary devices of the two support arms which are assigned to one another always rotate anticlockwise about this angle. In an example with two pairs of rotary devices, provision can be made in a basic position in which the central beam runs from the x-ray emitter to the x-ray detector in a vertical direction, for at least one pair of rotary devices assigned to axes of rotation to run in the horizontal direction and at least one pair of rotary devices assigned to axes of rotation to run in a direction which is tilted by 45 degrees from the vertical.

It is expedient if the rotary devices assigned to one another can optionally be coupled and decoupled by a switching facility. Provision can then be made particularly advantageously for the rotary devices to be decouplable in order to bring the support arm into a parking position. This is advantageous if for instance the x-ray facility is arranged in a surgical operation environment, in which, for access to the patient, the support arms are to be moved into the parking position which is least bothersome. For such purposes, decoupling of the rotary devices assigned to one another is conceivable and advantageous. The coupling and decoupling, just as incidentally also the movements per se, can take place automatically and/or manually, this being examined in greater detail below.

In a particularly preferred embodiment of the present invention, provision can be made for each support arm to contain at least two semi-circular segments, which can be rotated counter to one another by the rotary devices. It is therefore possible to finally embody the support arms in a semi-circular manner, wherein they are composed of various segments, which each cover a specific angular range, in particular an angular range between 1 degree and 179 degree for one segment. A particularly simple, stable and space-saving embodiment is produced in this way, since with semi-circular segments, it is very easy to ensure by mechanical measures the best possible mobility of the segments counter to one another. With the present invention, a situation results in which the x-ray emitter and x-ray detector, preferably coupled, can be moved on a spherical surface. It should be noted again at this point that if an additional axis of rotation is provided directly on the x-ray emitter and x-ray detector, an extension to ellipsoid surfaces is also conceivable.

It is particularly advantageous here if all segments cover an identical angle. In particular, with a support arm containing two segments, provision can be made for each segment to cover half of the overall angle that the support arm covers. It is particularly advantageous for the overall angle, if the support arm covers an angle of 90 degrees or more, in particular 120 degrees to 130 degrees. If the support arms are rotatably mounted on a stand for instance about a first pair of axes of rotation by a corresponding rotary device and the segments also cover a similar angle, at an angle of 90 Grad for instance 45 degrees respectively, at an angle of 120 degrees for instance 60 degrees respectively, a mutual rotation of the x-ray emitter and of the x-ray detector about an object to be recorded by 180 degrees about any axis is therefore possible at an overall angle of 90 degrees, with a support arm covering a larger angle than 90 degrees, this being particularly advantageous in respect of the three-dimensional imaging.

As already mentioned, it may be expediently conceivable for the support arms to be arranged on a stand running vertically in each instance, in particular rotatably about a rotary device counter to the stand. This is particularly important in support arms including semi-circular segments, wherein the height of the stand is selected here such that the support arm can advantageously be completely rotated about the corresponding rotary device, without touching the base. The corresponding rotary axes of the assigned pair of rotary devices, which couple the support arm to the stand respectively, expediently run here in a horizontal direction so that the position of the stand, to which the support arms are coupled, essentially also corresponds to the height of the isocenter.

It is advantageous in this context if a parking facility is provided for pivoting the support arm about a vertical axis around the stand in order to bring the support arm into a parking position. Such a parking facility and/or pivoting facility therefore enables for instance, if access to a patient couch is required during an intervention or suchlike, the support arm to be moved the intervention area in a simple manner into a parking position.

Provision can also be made for the stand to have a height-adjusting facility, wherein the height-adjusting facilities are or can be coupled in particular such that only the same height adjustments are possible for the stand. The stands and/or columns, on which the support arms, in particular the semi-circular segments are arranged, can consequently also be made height-adjustable in order to change the height of the isocenter or suchlike for instance. This provides for a further degree of freedom which increases flexibility and is easy to realize.

It is also conceivable to provide for a distance-changing facility for changing the distance between the stands, which is moveably coupled to a tilting facility for the x-ray facility for the x-ray emitter and the x-ray detector. This therefore means that in an instance in which the x-ray emitter and the x-ray detector can be tilted, it is also conceivable to change the distance between the stands and consequently furthermore to define an isocenter, through which the axes of rotation pass.

In a further embodiment of the present invention, provision can be made for the x-ray emitter and x-ray detector to be fastened to the support arm by way of a rotary device for rotation about an axis corresponding to the central beam. Rotary devices can therefore also be provided which allow for rotation about an axis of rotation corresponding to the central beam, wherein provision can also be made here to enable an independent rotatability of the x-ray emitter and x-ray detector counter to one another or only to provide the x-ray emitter or x-ray detector with such a rotary device. A movement coupling facility can also exist here.

Provision can further be made for the x-ray emitter and/or the x-ray detector to be fastened on the support arm by way of a linear adjusting device for variable distancing from the support arm. A detector lift and/or a tube lift can therefore also be provided, so that the distance from the isocenter can likewise be changed. These adjusting devices can be embodied to be coupled to one another so that a type of mechanical "zoom" is finally enabled in respect of the isocenter.

The rotary device may for instance be embodied as swivel hinges, but other possibilities for twisting components counter to one another are however essentially also possible.

A drive device for automatically adjusting the rotary device can advantageously be assigned to at least one part of the rotary device, preferably all rotary devices. It is also possible in this way to enable an automatic adjustment, into which the corresponding coupling facilities are also integrated. It is precisely in this context that it is particularly advantageous if the x-ray facility has a control facility, which is embodied to control the drive device for automatically moving into a target recording geometry. If switchable motion coupling facilities are provided, the control facility can naturally also be embodied to control the same. Other adjustment options which are also available, for instance the cited adjusting device, parking facilities and suchlike, can be controlled accordingly by the control facility, which can coordinate the entire mobility of the x-ray facility. The control facility can be coupled to an operating facility, by way of which target recording geometries can be input and/or the procedure can be arranged in a parking position, which can naturally also be controlled by way of a control facility. Automation of the flexible, reproducible and stable mobility of the x-ray facility is possible overall in this way.

The x-ray facility can be embodied as a mobile x-ray facility which can be run on rails or can be mounted on a ceiling. Other types of stationary x-ray facilities are also conceivable in addition to a ceiling support. In order to realize a mobile x-ray facility, a rail system can be provided for instance, on which the stand can be moved with the support arm and suchlike. In this way a distance-changing facility, as already discussed above, can also be realized.

Other features which are considered as characteristic for the invention are set forth in the appended claims.

Although the invention is illustrated and described herein as embodied in an X-ray facility having a recording arrangement held on support arms, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE INVENTION

Figure 1:
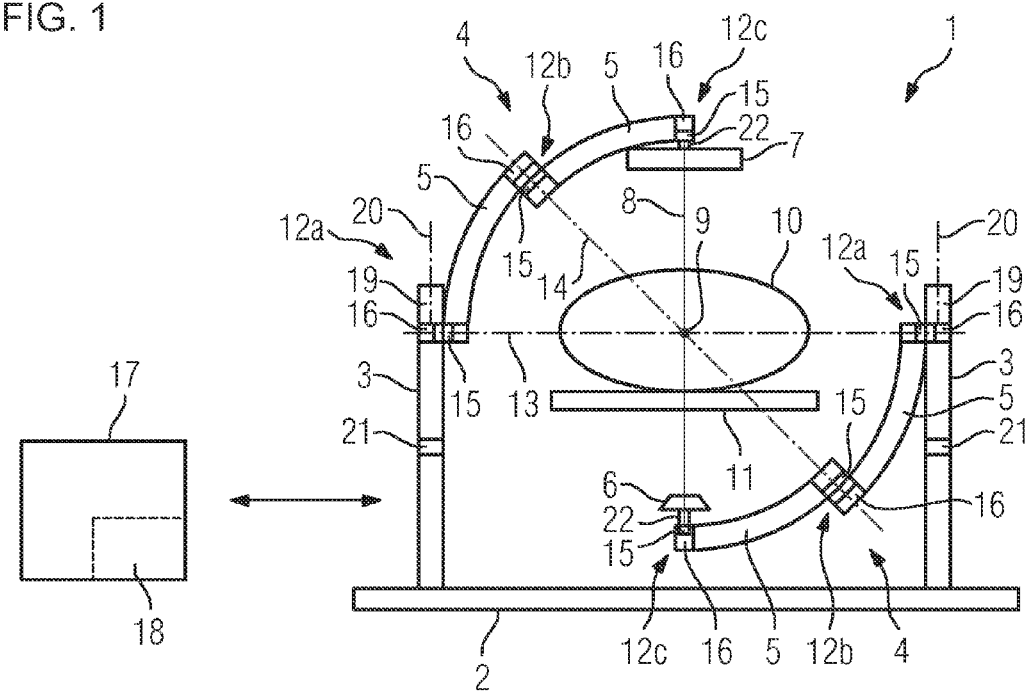
FIG. 1 is an illustration of an a first embodiment of an x-ray facility according to the invention.

FIG. 1 shows a first exemplary embodiment of an inventive x-ray facility 1, which is currently embodied as a mobile x-ray facility 1. To this end, it includes two stands 2 in the present exemplary embodiment which are coupled and guided in a rail system 2, each of which contains a support arm 4 consisting of semicircular segments 5. An x-ray emitter 6 and x-ray detector 7 are arranged at the end of the support arm 4. A central beam 8 from the x-ray emitter 6 to the x-ray detector 7, which is embodied here as a flat panel detector, traverses an isocenter 9, as is essentially known, which is disposed within an object 10 to be recorded, here a patient, in order to execute x-ray recordings.

The x-ray facility 1 is currently provided for use in a surgical operation environment, which also includes a patient couch 11, by way of which the isocenter 9 is currently arranged in the basic position shown.

It is apparent that the support arms 4 are coupled to the stands 3 by way of rotary devices 12a, which allow a rotation of the support arm 4 counter to the stand 3 about an axis of rotation 13, assigned to one another, which is same for both rotary devices 12a, the axis of rotation 13 crossing the isocenter. The segments 5 are coupled to one another by way of a rotary device 12b in each instance, which allow for a rotation of the segments 5 counter to one another about an axis of rotation 14, which in turn is identical for both rotary devices 12b of both support arms 4 and runs through the isocenter 9. A further possibility of rotation is produced by the rotary devices 12c, by which the x-ray detector 7 and the x-ray emitter 6 are coupled to the end of the support arm 4. A rotation about the central beam 8 as an axis of rotation is possible there.

A translational movement of the x-ray emitter 6 and x-ray detector 7 on a spherical surface is possible by the rotary devices 12a, 12b. Different recording geometries can consequently be assumed. This applies particularly if the rotary devices 12a, 12b and 12c associated with one another are coupled to one another such that when the one rotary device 12a, 12b is rotated about a specific angle, the other rotary device 12a, 12b is rotated in the same direction about the specific angle.

Swivel hinges 15 are in each case currently provided as the rotary devices. These can be automatically adjusted, wherefore a drive device 16 is assigned in each instance. The drive devices 16 can be controlled by way of a central control facility 17 of the x-ray facility 1, which also includes an integrated movement coupling facility (controller) 18, by the movements optionally taking place in a coupled or uncoupled manner, with a decoupling taking place for instance when moving into a parking position with respect to the rotary devices 12a, 12b. Otherwise, the rotary devices 12a, 12b and/or the drive devices 16 assigned thereto are always controlled such that the isocenter 9 and a central beam 8 are preserved, consequently x-ray recordings can be actuated.

In the present exemplary embodiment, each support arm 4 covers an angle of 90 degrees, each segment an angle of 45 degrees, in other words half. This enables almost all recording geometries to be run, wherein a rotation up to 180 degrees about the isocenter 9 is also possible about any axes of rotation by the recording arrangement. Embodiments in which each support arm covers for instance 120 degrees and each segment 60 degrees for instance are also conceivable, wherein rotations of the recording arrangement exceeding 180 degrees are also conceivable.

The x-ray facility 1 contains still further adjustment options in order to increase flexibility, wherein, as is apparent, the basic capture of recording geometries in the present example can apparently be realized in a predominantly stable and reproducible manner by rotating the rotary devices 12a, 12b. A parking facility 19 is currently also provided, by way of which the support arm 4 can also be pivoted about a vertical axis 20 opposite the stand 3 so that it can be brought into a parking position (not shown here) which is remote from the patient couch.

A height-adjusting apparatus 21, for instance a telescopic facility, is also provided on the stands 4, which allows for a height adjustment of the stand 3, wherein by correspondingly controlling the height-adjusting apparatus 21, both stands 3 can be adjusted equally in terms of their height so that the height of the isocenter 9 can be adjusted in particular as a function of the object to be recorded concretely.

The exemplary embodiment according to FIG. 1 further contains adjusting devices 22 both on the x-ray emitter 6 and also on the x-ray detector 7, by way of which these can be moved linearly, so that the distance to the isocenter 9 can change if necessary. The adjusting devices can also be controlled, in particular coupled, by way of the control facility 17.

It should be noted again at this point, although it is not shown in further detail, that the rail system 2 can also be used as a distance-changing facility for the stand 3, wherein the functionality of the x-ray facility 1 can also be maintained with a changed distance, if a corresponding tilting facility exists for the x-ray emitter and the x-ray detector so that a new suitable isocenter 9 is formed, through which the axes of rotation 13, 14 and the central beam 9 run.

Not shown in further detail is a control facility, by way of which recording geometries required by a user, if necessary also concrete movements, can be predetermined, which are then converted by the control facility 17 into corresponding control commands for the drive device 16 and other drive devices of the remaining adjusting options. Selection of the parking position is also converted into corresponding commands by the control facility 18. Suitable control elements may be available herefor.

Figure 2:
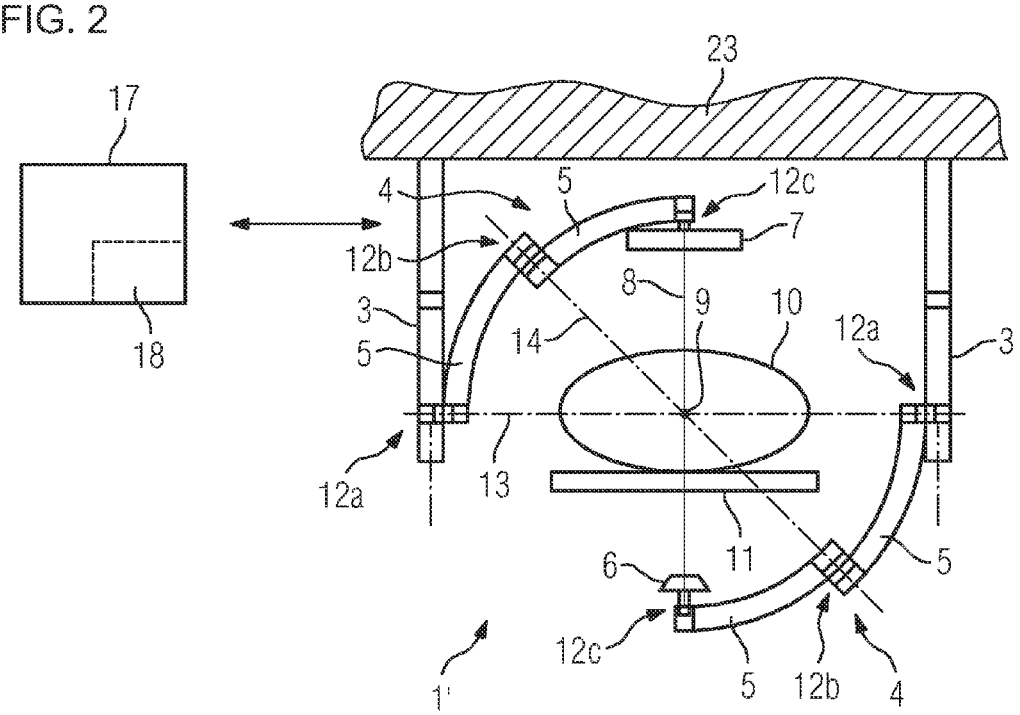
FIG. 2 is an illustration of a second embodiment of the x-ray facility.

FIG. 2 shows a modified exemplary embodiment of an inventive x-ray facility 1'. By contrast with FIG. 1, the x-ray facility 1' here is assembled on a ceiling 23, in other words this is a stationary x-ray facility 1', the stand 3 of which is immovably connected to the ceiling 23. The remaining components are identical to those in FIG. 1.

Although the invention was illustrated and described in more detail by the preferred exemplary embodiment, the invention is not restricted by the disclosed examples and other variations can be derived herefrom by the person skilled in the art without departing from the scope of protection of the invention.

The invention claimed is:

1. An x-ray facility, comprising:
   at least an x-ray emitter;
   an x-ray detector and an isocenter disposed along a central beam path between said x-ray emitter and said x-ray detector;
   support arms, each of said x-ray emitter and said x-ray detector disposed on separate ones of said support arms; and
   rotary devices, at least one of said rotary devices disposed on each of said support arms, by way of said rotary devices said x-ray emitter and said x-ray detector can be rotated about an axis of rotation intersecting said isocenter and not corresponding to said central beam path, wherein axes of rotation match said rotary devices assigned to one another on different ones of said support arms.

2. The x-ray facility according to claim 1, further comprising at least one movement coupling facility for controlling at least one pair of said rotary devices, which upon rotation of said one rotary device about a specific angle is embodied to rotate said other rotary devices in a same direction about the specific angle.

3. The x-ray facility according to claim 2, wherein said rotary devices include at least two pairs of coupled rotary devices provided with axes of rotation pointing in different directions.

4. The x-ray facility according to claim 2, wherein said rotary devices assigned to one another can be coupled and decoupled by a switching facility, and can be decoupled for bringing said at least one of said support arms into a parking position.

5. The x-ray facility according to claim 1, wherein each of said support arms contains at least two semi-circular segments, which can be rotated counter to one another by means of one of said rotary devices.

6. The x-ray facility according to claim 5, wherein all of said semi-circular segments cover an identical angle.

7. The x-ray facility according to claim 5, wherein each of said support arms covers an angle in a range of 120° to 130°.

8. The x-ray facility according to claim 5, wherein each of said support arms covers an angle of at least 90°.

9. The x-ray facility according to claim 1, further comprising a stand, said support arms are disposed on said stand running vertically in each instance.

10. The x-ray facility according to claim 9, further comprising a parking facility to pivot at least one of said support arms about a vertical axis around said stand to bring said at least one of said support arms into a parking position.

11. The x-ray facility according to claim 9,
    further a tilting facility;
    wherein said stand is one of a plurality of stands;
    wherein at least one of said stands includes at least one of:
       a height adjustment facility, wherein said height adjustment facility can be coupled such that only identical height adjustments are possible for said stand; or
       a distance changing facility for changing a distance between said stands, which are movably coupled to said tilting facility for said x-ray emitter and said x-ray detector.

12. The x-ray facility according to claim 9, wherein said support arms are rotatable about said rotary devices counter to said stand.

13. The x-ray facility according to claim 1, wherein said x-ray emitter and said x-ray detector are fastened to said support arms by way of said rotary devices for rotation about an axis corresponding to said central beam path.

14. The x-ray facility according to claim 1, further comprising a linear adjusting device, at least one of said x-ray emitter or said x-ray detector is fastened to said support arms by way of said linear adjusting device at a variable distance from said support arms.

15. The x-ray facility according to claim 1,
    wherein at least one of said rotary devices is a swivel joint; and
    further comprising drive devices for automatically adjusting said rotary devices.

16. The x-ray facility according to claim 15, further comprising a control facility for controlling said drive devices for automatic driving of a targeted recording geometry.

17. The x-ray facility according to claim 1, further comprising rails and the x-ray facility can be moved on said rails.

18. The x-ray facility according to claim 1, wherein the x-ray facility is configured to be mounted to a ceiling.

* * * * *